United States Patent
Komiya et al.

(10) Patent No.: US 9,494,768 B2
(45) Date of Patent: Nov. 15, 2016

(54) IMAGE CAPTURING MODULE AND IMAGE CAPTURING APPARATUS

(71) Applicant: OLYMPUS CORPORATION, Shibuya-ku, Tokyo (JP)

(72) Inventors: Yasuhiro Komiya, Kawaguchi (JP); Kosei Tamiya, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/549,315

(22) Filed: Nov. 20, 2014

(65) Prior Publication Data

US 2015/0077617 A1 Mar. 19, 2015

Related U.S. Application Data

(63) Continuation of application No. PCT/JP2013/063966, filed on May 20, 2013.

(30) Foreign Application Priority Data

Jun. 21, 2012 (JP) .................................. 2012-140082

(51) Int. Cl.
*H04N 5/335* (2011.01)
*G02B 13/00* (2006.01)
(Continued)

(52) U.S. Cl.
CPC ......... *G02B 13/0055* (2013.01); *A61B 5/0077* (2013.01); *A61B 5/1032* (2013.01);
(Continued)

(58) Field of Classification Search
CPC .......... G02B 13/0055; G02B 27/1013; H04N 9/045; H04N 5/2358; G01J 3/2823; G01J 2003/2826; G01J 3/513; G01J 3/36; A61B 5/0077; A61B 5/1032
USPC ................. 348/335, 336, 272, 273, 278–280
See application file for complete search history.

(56) References Cited

U.S. PATENT DOCUMENTS

| 8,228,417 B1 * | 7/2012 | Georgiev | G03B 11/00 348/335 |
| 2001/0039061 A1 | 11/2001 | Suzuki et al. | |

(Continued)

FOREIGN PATENT DOCUMENTS

| JP | 2001160973 A | 6/2001 |
| JP | 2002135796 A | 5/2002 |

(Continued)

OTHER PUBLICATIONS

International Search Report dated Aug. 20, 2013 issued in International Application No. PCT/JP2013/063966.

(Continued)

*Primary Examiner* — Sinh Tran
*Assistant Examiner* — Zhenzhen Wu
(74) *Attorney, Agent, or Firm* — Holtz, Holtz & Volek PC

(57) ABSTRACT

Provided is an image capturing module including a microlens array that collects light from a subject, which is imaged at an image plane; a filter that allows light in specific wavelength bands in the collected light to pass therethrough; and an image capturing device that acquires images of the light passing through the filter, wherein the filter is formed by arraying a plurality of RGB filter portions and a plurality of narrow-band filter portions, the image capturing device includes a plurality of color-wavelength obtaining regions and a plurality of narrow-band-wavelength obtaining regions, and the microlens array includes a plurality of first microlenses corresponding to the respective color-wavelength obtaining regions and a plurality of second microlenses corresponding to the respective narrow-band-wavelength obtaining regions, and the first microlenses are each disposed so that the light from the subject imaged at the image plane reaches at least one of the color-wavelength obtaining regions.

12 Claims, 13 Drawing Sheets

(51) Int. Cl.
- *G01J 3/36* (2006.01)
- *A61B 5/00* (2006.01)
- *A61B 5/103* (2006.01)
- *G01J 3/51* (2006.01)
- *G01J 3/28* (2006.01)
- *G01J 3/02* (2006.01)
- *G02B 27/10* (2006.01)
- *H04N 5/235* (2006.01)
- *H04N 9/04* (2006.01)

(52) U.S. Cl.
CPC ........... *G01J 3/0208* (2013.01); *G01J 3/2823* (2013.01); *G01J 3/36* (2013.01); *G01J 3/513* (2013.01); *G02B 27/1013* (2013.01); *H04N 5/2358* (2013.01); *H04N 9/045* (2013.01); *A61B 2562/0233* (2013.01); *G01J 2003/2826* (2013.01); *H04N 2209/047* (2013.01)

(56) References Cited

U.S. PATENT DOCUMENTS

| | | | |
|---|---|---|---|
| 2008/0007839 A1* | 1/2008 | Deng | G02B 3/0018 359/642 |
| 2008/0123097 A1 | 5/2008 | Muhammed et al. | |
| 2008/0135899 A1* | 6/2008 | Park | H01L 27/14621 257/294 |
| 2009/0086323 A1 | 4/2009 | Nobuyuki | |
| 2009/0225277 A1 | 9/2009 | Gil | |
| 2011/0226934 A1 | 9/2011 | Tian et al. | |
| 2011/0228144 A1 | 9/2011 | Tian et al. | |
| 2013/0235256 A1 | 9/2013 | Kodama | |

FOREIGN PATENT DOCUMENTS

| | | | |
|---|---|---|---|
| JP | 2003087806 A | | 3/2003 |
| JP | 2004228662 A | | 8/2004 |
| JP | 2006084425 A | | 3/2006 |
| JP | 2006140767 A | | 6/2006 |
| JP | 2006270356 A | * | 10/2006 |
| JP | 2008518229 A | | 5/2008 |
| JP | 2009080356 A | | 4/2009 |
| JP | 2011182237 A | | 9/2011 |
| WO | 2011116268 A1 | | 9/2011 |
| WO | 2012066741 A1 | | 5/2012 |

OTHER PUBLICATIONS

Japanese Office Action (and English translation thereof) dated Mar. 1, 2016, issued in counterpart Japanese Application No. 2012-140082.

* cited by examiner

US 9,494,768 B2

IMAGE CAPTURING MODULE AND IMAGE CAPTURING APPARATUS

CROSS-REFERENCE TO RELATED APPLICATIONS

This is a continuation of International Application PCT/JP2013/063966, with an international filing date of May 20, 2013, which is hereby incorporated by reference herein in its entirety. This application claims the benefit of Japanese Patent Application No. 2012-140082, filed on Jun. 21, 2012, the content of which is incorporated herein by reference.

TECHNICAL FIELD

The present invention relates to an image capturing module and an image capturing apparatus.

BACKGROUND ART

In the related art, there is a known technology for extracting a characteristic spectrum of skin conditions and so forth by using a 16-band multispectral camera (for example, see Patent Literature 1). With this technology, it is possible to ascertain subtle color changes that are difficult to distinguish with the human eye.

Specifically, with the technology in Patent Literature 1, image acquisition of a wide-band image and a narrow-band image is performed using a digital camera for RGB color image acquisition. In this case, although an RGB image can be readily obtained, for a narrow-band image, the image acquisition takes time because illumination light of different colors is radiated sequentially. Thus, when acquiring an image of a moving subject, the shape of the subject changes between the RGB image and the narrow-band image, or between narrow-band images.

CITATION LIST

Patent Literature

{PTL 1}
Japanese Unexamined Patent Application, Publication No. 2006-84425

SUMMARY OF INVENTION

An aspect of the present invention is an image capturing module including a microlens array that collects light from a subject, which is imaged at an image plane; a filter that allows light in specific wavelength bands in the light collected by the microlens array to pass therethrough; and an image capturing device that acquires images of the light passing through the filter, wherein the filter is formed by arraying a plurality of RGB filter portions that pass light in RGB wavelength bands and a plurality of narrow-band filter portions that pass light in wavelength bands that are narrower than the RGB wavelength bands, the image capturing device includes a plurality of color-wavelength obtaining regions that acquire images of the light passing through the RGB filter portions and a plurality of narrow-band-wavelength obtaining regions that acquire images of the light passing through the narrow-band filter portions, and the microlens array includes a plurality of first microlenses that are disposed in correspondence with the respective color-wavelength obtaining regions and a plurality of second microlenses that are disposed in correspondence with the respective narrow-band-wavelength obtaining regions, and the first microlenses are each disposed so that the light from the subject imaged at the image plane reaches at least one of the color-wavelength obtaining regions.

DESCRIPTION OF EMBODIMENT

An image capturing module 1 and an image capturing apparatus 10 according to an embodiment of the present invention will be described below with reference to the drawings.

Figure 1:
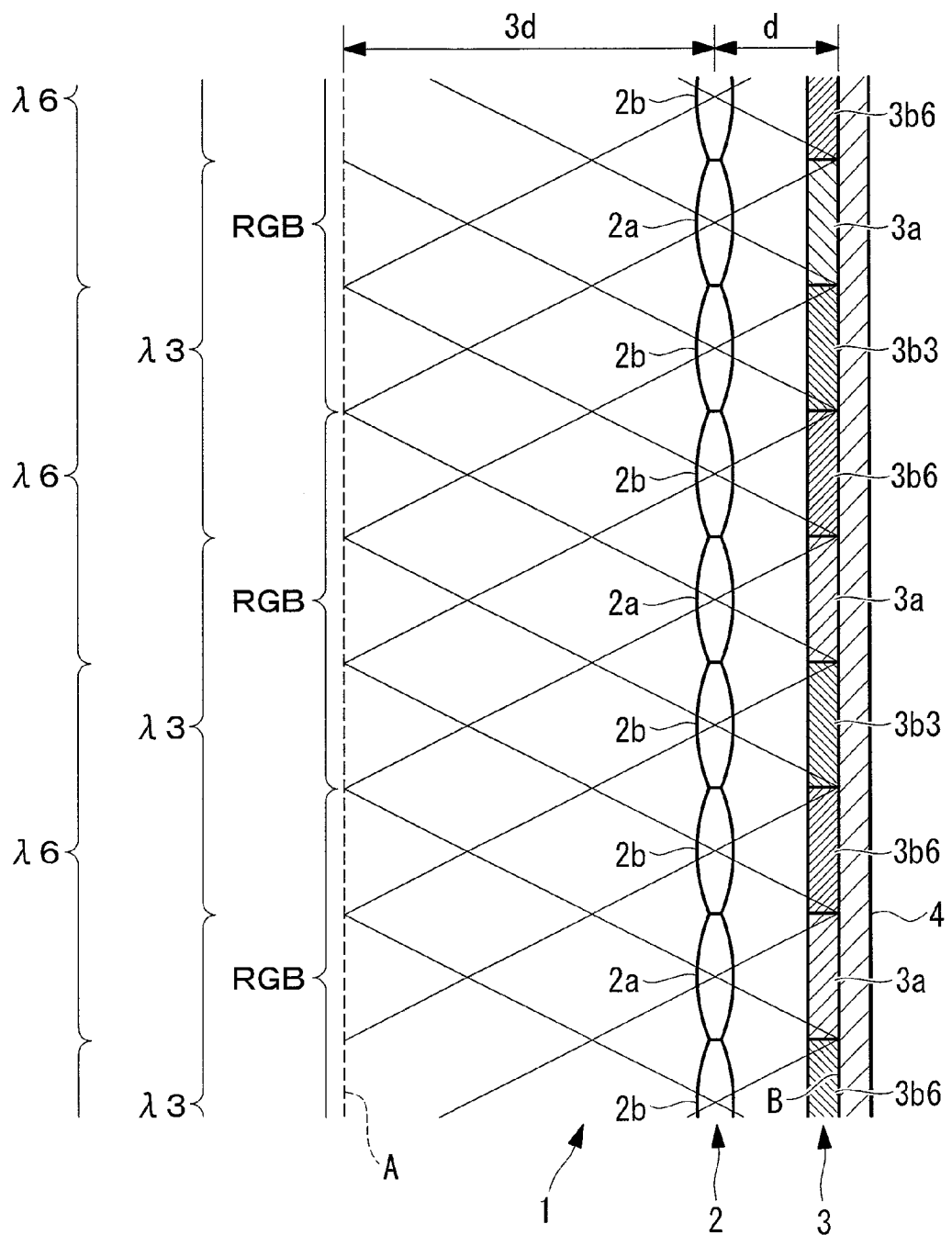
FIG. 1 is a longitudinal sectional view showing an image capturing module according to an embodiment of the present invention.

As shown in FIG. 1, the image capturing module 1 according to this embodiment includes a microlens array 2, a filter 3, and an image capturing device 4.

Figure 2:
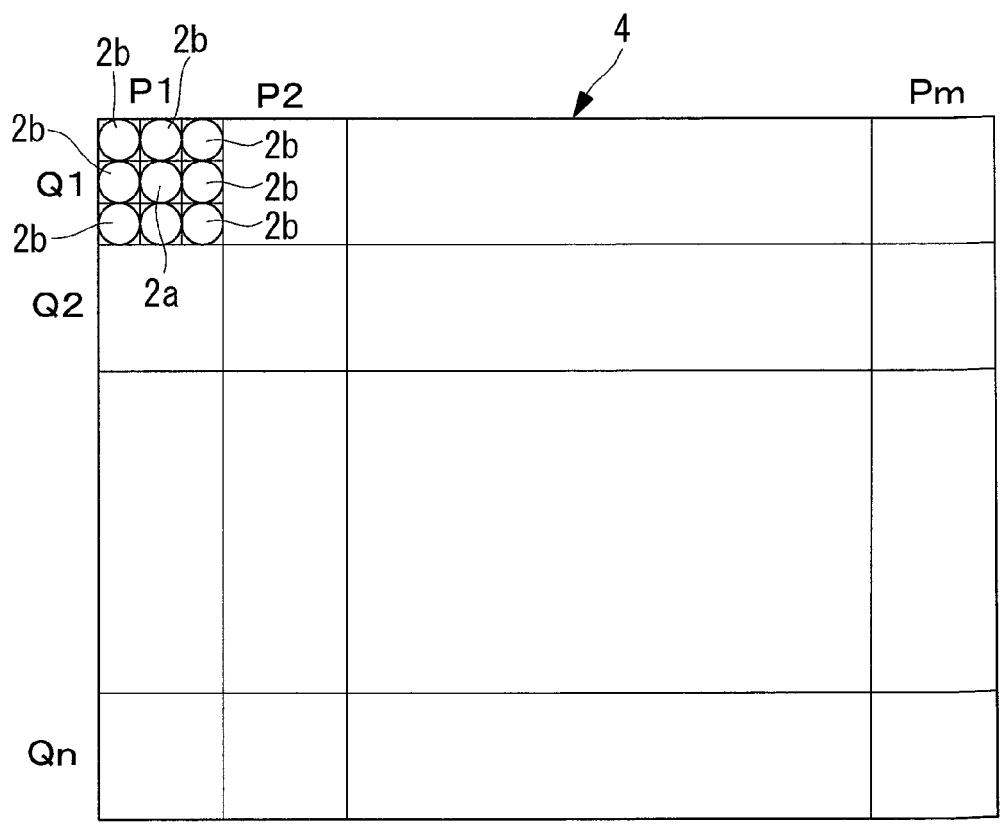
FIG. 2 is a front view for explaining an image capturing device and an array of image-capturing region units and microlenses in the image capturing module in FIG. 1.
Figure 3:
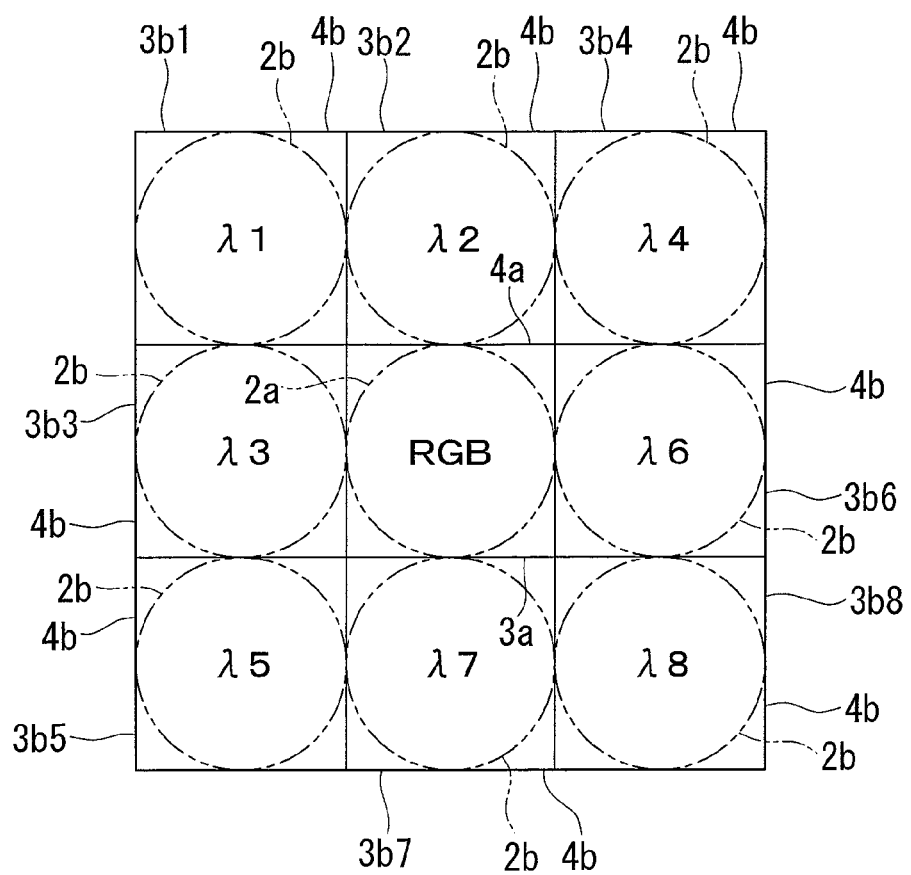
FIG. 3 is a diagram for explaining the relationship between the image-capturing region unit and the microlenses in FIG. 2.

As shown in FIG. 2, the image capturing device 4 is divided into m×n image-capturing region units (PiQj: i=1 to m, j=1 to n, where m and n are integers), and each image-capturing region unit PiQj is further divided into 3×3=9 partial regions 4a and 4b, as shown in FIG. 3. In the respective partial regions 4a and 4b, microlenses (first microlens 2a and second microlenses 2b) are disposed in correspondence with the partial regions 4a and 4b.

In the example shown in FIG. 3, in all of the image-capturing region units PiQj in the image capturing device 4, the center partial region 4a is a color-wavelength obtaining region that acquires an image of light in RGB wavelength bands (hereinafter referred to as color-wavelength obtaining region 4a), and the eight partial regions 4b surrounding the color-wavelength obtaining region 4a are narrow-band-wavelength obtaining regions that respectively acquire images of light in eight wavelength bands λ1 to λ8, which are sufficiently narrower than the RGB wavelength bands (hereinafter referred to as narrow-band-wavelength obtaining regions 4b). In each image-capturing region unit PiQj, it is not necessary to dispose the color-wavelength obtaining region 4a at the center, and it may be disposed at any position.

As described above, the microlens array 2 includes a plurality of microlenses 2a and 2b having the same optical characteristics, which are arrayed in correspondence with all of the partial regions 4a and 4b in the image capturing device 4. If it is assumed that each of the partial regions 4a and 4b is formed of, for example, 50×50 pixels, in the case where a 12-million-pixel image capturing device 4 is used, m 26 and n=20, and the total number of microlenses 2a and 2b is 26×20×3×3=4680.

The individual microlenses 2a and 2b that constitute the microlens array 2 have a reduction factor of 3, as shown in FIG. 1. Thus, between an image plane A of an image capturing lens, to be described later, and an image-capturing plane B of the image capturing device 4, the microlenses 2a and 2b are disposed a distance d away from the image capturing plane B and a distance 3d away from the image plane A.

The filter 3 includes RGB filter portions 3a that cover the color-wavelength obtaining regions 4a of the image capturing device 4 and narrow-band filter portions 3b1 to 3b8 that respectively cover the other eight narrow-band-wavelength obtaining regions 4b.

Figure 4:
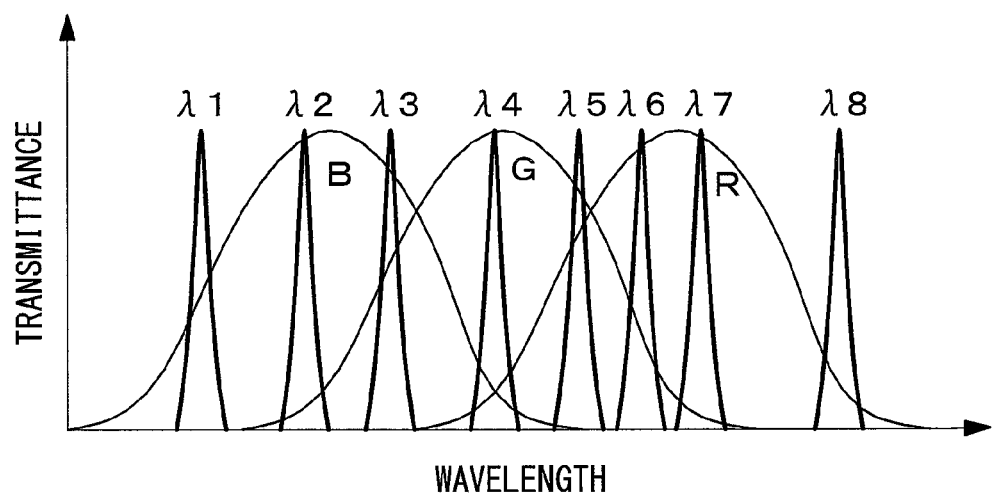
FIG. 4 is a diagram showing the transmittance characteristics of RGB filter portions and narrow-band filter portions in a filter of the image-capturing module in FIG. 1.
Figure 5:
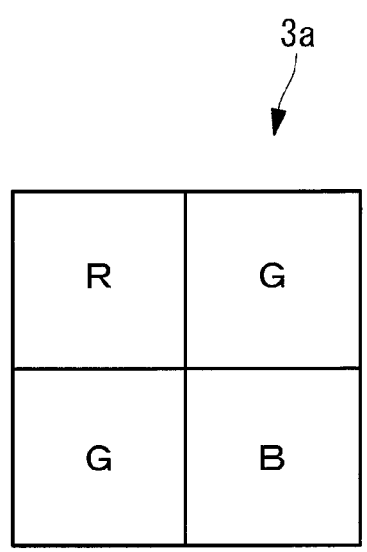
FIG. 5 is a diagram showing an RGB Bayer array as an example of the RGB filter portions in the filter of the image-capturing module in FIG. 1.

As shown in FIG. 5, in the RGB filter portion 3a, red (R), green (G), and blue (B) color filters are disposed in the form of 2×2 neighboring pixels, thus forming a so-called RGB Bayer array filter. As shown in FIG. 4, the filters of each color are configured so as to transmit light in comparatively wide wavelength bands.

The narrow-band filter portions 3b1 to 3b8 are provided with reflective films (not illustrated) on the two flat surfaces thereof, which are disposed parallel to each other with a gap therebetween, thus forming spectral filters known as etalons, and as shown in FIG. 4, are configured so as to be capable of selectively transmitting light in extremely narrow wavelength bands λ1 to λ8, and so that the wavelength bands that are transmitted can be made different depending on the gap between the reflective films. The narrow-band filter portions 3b1 to 3b8 respectively disposed in the eight narrow-band-wavelength obtaining regions 4b are configured so as to respectively transmit light in the different wavelength bands λ1 to λ8 by, for example, making the gaps between the reflective films different.

The operation of the thus-configured image capturing module 1 according to this embodiment will be described below.

In the image capturing module 1 according to this embodiment, since the image-capturing region units PiQj formed of the 3×3 partial regions 4a and 4b are repeatedly arrayed in the row direction and the column direction, the filter portions 3a and 3b1 to 3b8 of the same kind, which transmit light in the same wavelength band, are disposed at a three-filter period in both the row direction and the column direction. Thus, since the reduction factors of the microlenses 2a and 2b are set to 3, as shown in FIG. 1, the light from the subject, which is imaged at the image plane A of the image capturing lens, arrives at every one of the wavelength obtaining regions 4a and 4b, for the filter portions 3a and 3b1 to 3b8 of all kinds (in FIG. 1, wavelength bands λ3 and λ6 and RGB are shown, but the others are omitted).

As a result, it is possible to prevent losses from occurring in partial images of the subject imaged at the neighboring wavelength obtaining regions 4a and 4b of the same kind. In other words, by combining partial images of the subject obtained by each of the color-wavelength obtaining regions 4a, it is possible to obtain a lossless RGB image signal of the entire image of the subject imaged at the image plane A of the image capturing lens. In addition, by combining partial images of the subject obtained by each of the narrow-band-wavelength obtaining regions 4b of the wavelength bands λ1 to λ8, it is possible to obtain eight lossless narrow-band image signals of the entire image of the subject imaged at the image plane A of the image capturing lens.

Thus, with the image capturing module 1 according to this embodiment, since the image of the subject imaged at the image plane A of the image capturing lens is split into a plurality of partial images by the microlens array 2 and multiple images are obtained by the plurality of wavelength obtaining regions 4a and 4b of the image capturing device 4, it is possible to simultaneously obtain an RGB image and narrow-band images of the subject; as a result, an advantage is afforded in that, when this RGB image and narrow-band images are combined, it is possible to obtain a clear blur-free image, even for a moving subject.

Next, an image capturing apparatus 10 that is provided with the image capturing module 1 according to the above-described embodiment will be described below with reference to the drawings.

Figure 6:
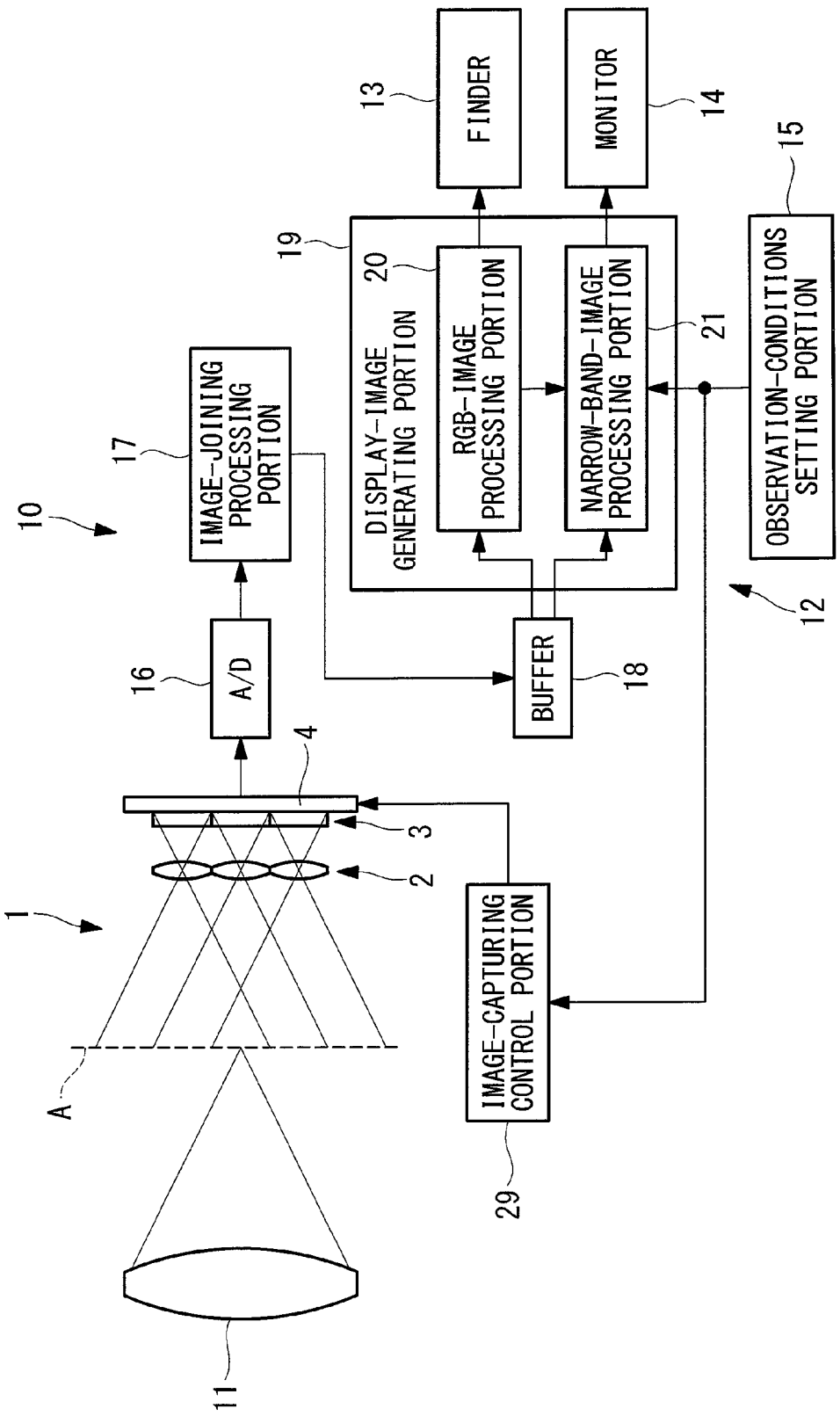
FIG. 6 is a diagram showing the overall configuration of an image capturing apparatus according to an embodiment of the present invention, which is provided with the image capturing module in FIG. 1.

As shown in FIG. 6, the image capturing apparatus 10 according to this embodiment includes an image capturing lens 11 that forms an image at the image plane A by focusing light coming from the subject; the above-described image capturing module 1; an image processing portion 12; a finder 13; a monitor 14; and an observation-conditions setting portion 15.

The image processing portion 12 includes an A/D converter 16 that converts an image signal formed of an analog signal obtained by the image capturing device 4 of the image capturing module 1 to a digital signal; an image-joining processing portion (RGB-image-information creating portion, narrow-band-image-information creating portion) 17 that creates RGB image information and eight items of narrow-band image information by joining image signals obtained by the same kind of wavelength obtaining regions 4a and 4b of the image capturing device 4; a buffer 18 that temporarily stores the created image information; and a display-image generating portion 19 that creates image information to be displayed, by using the image information stored in the buffer 18.

The display-image generating portion 19 includes an RGB-image processing portion 20 that processes the RGB image information and a narrow-band-image processing portion 21 that combines the RGB image information processed in the RGB-image processing portion 20 and the narrow-band image information.

The observation-conditions setting portion 15 is configured so that the observer can specify the image acquisition conditions for the image capturing device 4, such as the angle of view and the exposure, and the observation conditions, such as which narrow-band image information of the wavelength bands λ1 to λ8 among the eight items of narrow-band image information is to be combined.

Figure 7:
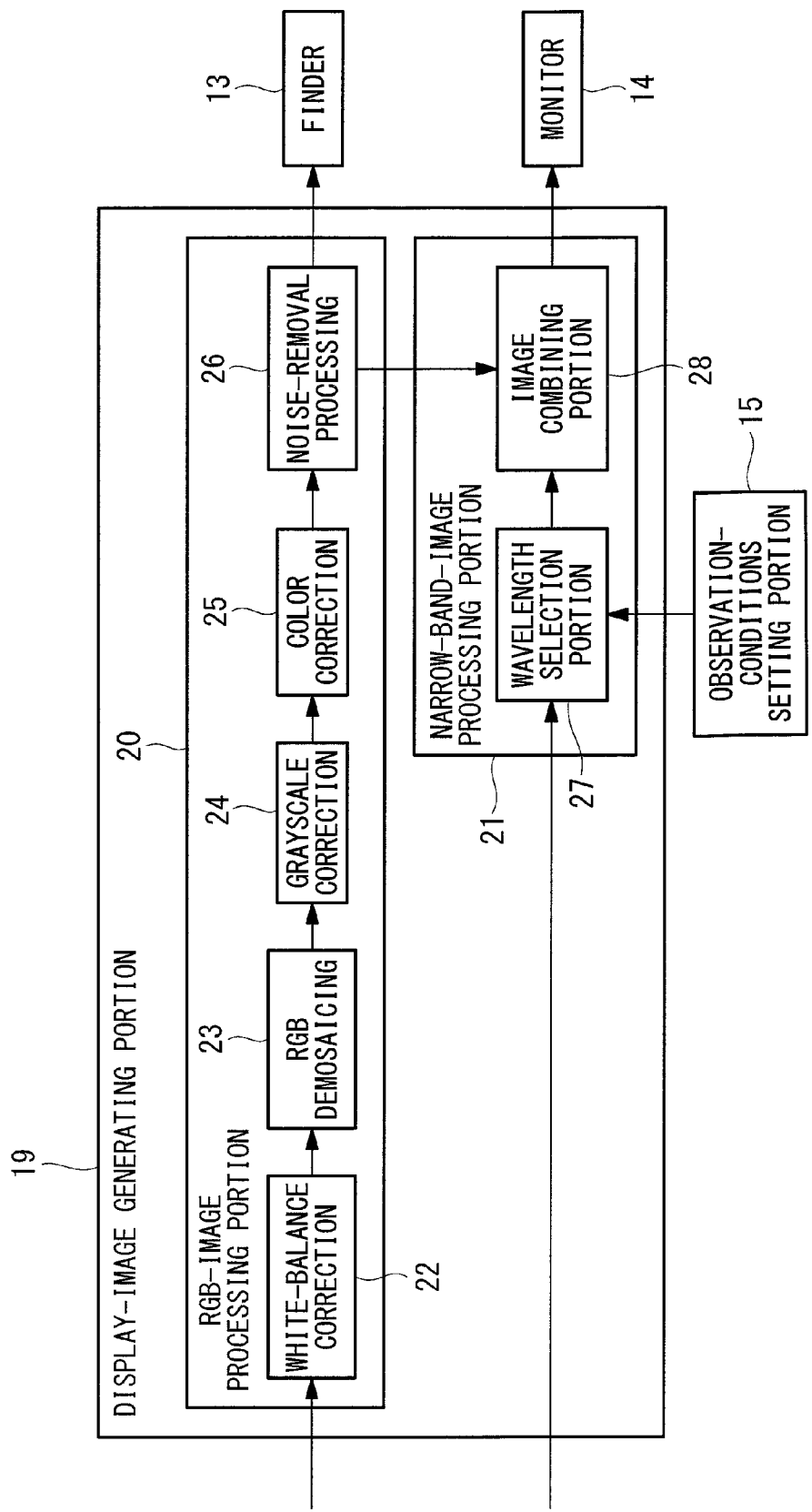
FIG. 7 is a block diagram for explaining the details of a display-image generating portion of the image capturing apparatus in FIG. 6.

As shown in FIG. 7, the RGB-image processing portion 20 includes a white-balance correction portion 22 that performs white-balance correction processing on the RGB image information sent from the buffer 18; an RGB demosaicing portion 23 that performs demosaicing processing; a grayscale correction portion 24 that performs grayscale correction processing; a color correction portion 25 that performs color correction processing; and a noise-removal processing portion 26 that performs noise-removal processing. The RGB image information processed in the RGB-image processing portion 20 is output to the finder 13 and the narrow-band-image processing portion 21.

The narrow-band-image processing portion 21 includes a wavelength selection portion 27 that selects the narrow-band image information for the wavelength band specified by the observation-conditions setting portion 15 and an image combining portion 28 that combines the narrow-band image information selected in the wavelength selection portion 27 and the RGB image information input from the RGB-image processing portion 20.

The combined image created in the image combining portion 28 is output to the monitor 14.

The finder 13, which is, for example, an electronic viewfinder, is provided in an eyepiece unit (not illustrated) and is configured to present the RGB image sent from the RGB-image processing portion 20 to the eye of the observer.

The operation of the thus-configured image capturing apparatus 10 according to this embodiment will be described below.

With the image capturing apparatus 10 according to this embodiment, after the light coming from the subject, which is focused by the image capturing lens 11, is imaged at the image plane A, it is collected by the microlens array 2 of the image capturing module 1 and is obtained by the plurality of wavelength obtaining regions 4a and 4b of the image capturing device 4 in the form of partial image signals of the subject, which overlap with each other.

The partial image signals of the subject, obtained by the image capturing device 4, are converted to digital signals by the A/D converter 16, whereupon, in the image-joining processing portion 17, they are joined together for each of the wavelength obtaining regions that obtained these partial image signals, thus creating the RGB image information and the eight items of narrow-band image information. The RGB image information created in the image-joining processing portion 17 is sent to the RGB-image processing portion 20 in the display-image generating portion 19, where various types of processing are performed thereon, and the RGB image information to be displayed is created. The created RGB image information is sent to the finder 13 and the narrow-band-image processing portion 21.

On the other hand, the narrow-band image information created in the image-joining processing portion 17 is sent to the narrow-band-image processing portion 21 in the display-image generating portion 19.

By displaying on the finder 13 the RGB image information sent to the finder 13, the observer can adjust the image acquisition conditions, such as the angle of view and the exposure. In addition, by using the observation-conditions setting portion 15, the observer selects one of the wavelength bands λ1 to λ8 that he or she wishes to observe in a superimposed manner on the RGB image.

In the observation-conditions setting portion 15, besides selection of the wavelength band for the narrow-band image to be observed in a superimposed manner on the RGB image, it is possible to specify whether to observe the RGB image without superimposing the narrow-band image thereon, or whether to observe only the selected narrow-band image, without superimposing the RGB image thereon.

The observation-conditions setting portion 15 is also connected to an image-capturing control portion 29 that controls the image capturing module 1, and, when the observation conditions are set via the observation-conditions setting portion 15, the image-capturing control portion 29 controls the image capturing module 1 so as to acquire an image of the subject with the set observation conditions, and an RGB image signal and narrow-band image signals are obtained. The obtained RGB image signal and narrow-band image signals are converted to digital signals by the A/D converter 16, and then the RGB image information and eight items of narrow-band image information are created in the image-joining processing portion 17 and are sent to the display-image generating portion 19.

In the display-image generating portion 19, the RGB image information is processed in the RGB-image processing portion 20 and is sent to the finder 13, and is also sent to the narrow-band-image processing portion 21. Also, in the narrow-band-image processing portion 21, when the wavelength band for the narrow-band image information to be superimposed is specified in the observation-conditions setting portion 15, the narrow-band image information corresponding to the specified wavelength band is selected in the wavelength selection portion 27.

Then, in the image combining portion 28, color processing, for example, for enhancement, is performed on the narrow-band image information selected in the wavelength selection portion 27, and the RGB image information sent from the RGB-image processing portion 20 is combined therewith. The combined image combined in the image combining portion 28 is output to the monitor 14 and is displayed thereon.

Figure 8A:
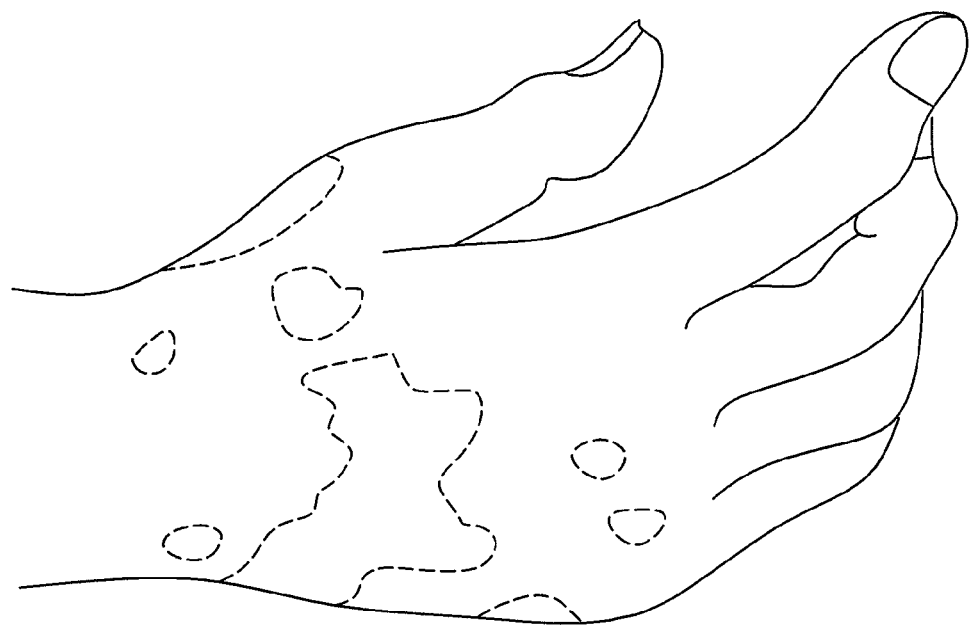
FIG. 8A is a diagram showing an example RGB image acquired by the image capturing apparatus in FIG. 6.
Figure 8B:
FIG. 8B is a diagram showing an example of a combined image acquired by the image capturing apparatus in FIG. 6, in which a narrow-band image and an RGB image are superimposed.

Schematic diagrams for the case where only the RGB image is displayed and the case where a narrow-band image of a prescribed wavelength band (for example, a center wavelength of 550 nm and a wavelength width of 10 nm) is enhanced and superimposed on the RGB image are shown in FIG. 8A and FIG. 8B, respectively. A skin condition that is not clear in the RGB image alone in FIG. 8A is clearly visible in FIG. 8B.

In this case, with the image capturing apparatus 10 according to this embodiment, since the RGB image signal constituting the RGB image information and the narrow-band image signal constituting the narrow-band image information are simultaneously obtained by the image capturing module 1, an advantage is afforded in that, even if these items of image information are superimposed, there is no positional shift between images, and it is possible to obtain a blur-free clear combined image. In addition, with the image capturing apparatus 10 according to this embodiment, since the RGB image information and the narrow-band image information are both obtained by the image-capturing module 1 without any loss, an advantage is afforded in that it is possible to observe the subject without overlooking any information about the subject.

Figure 9:
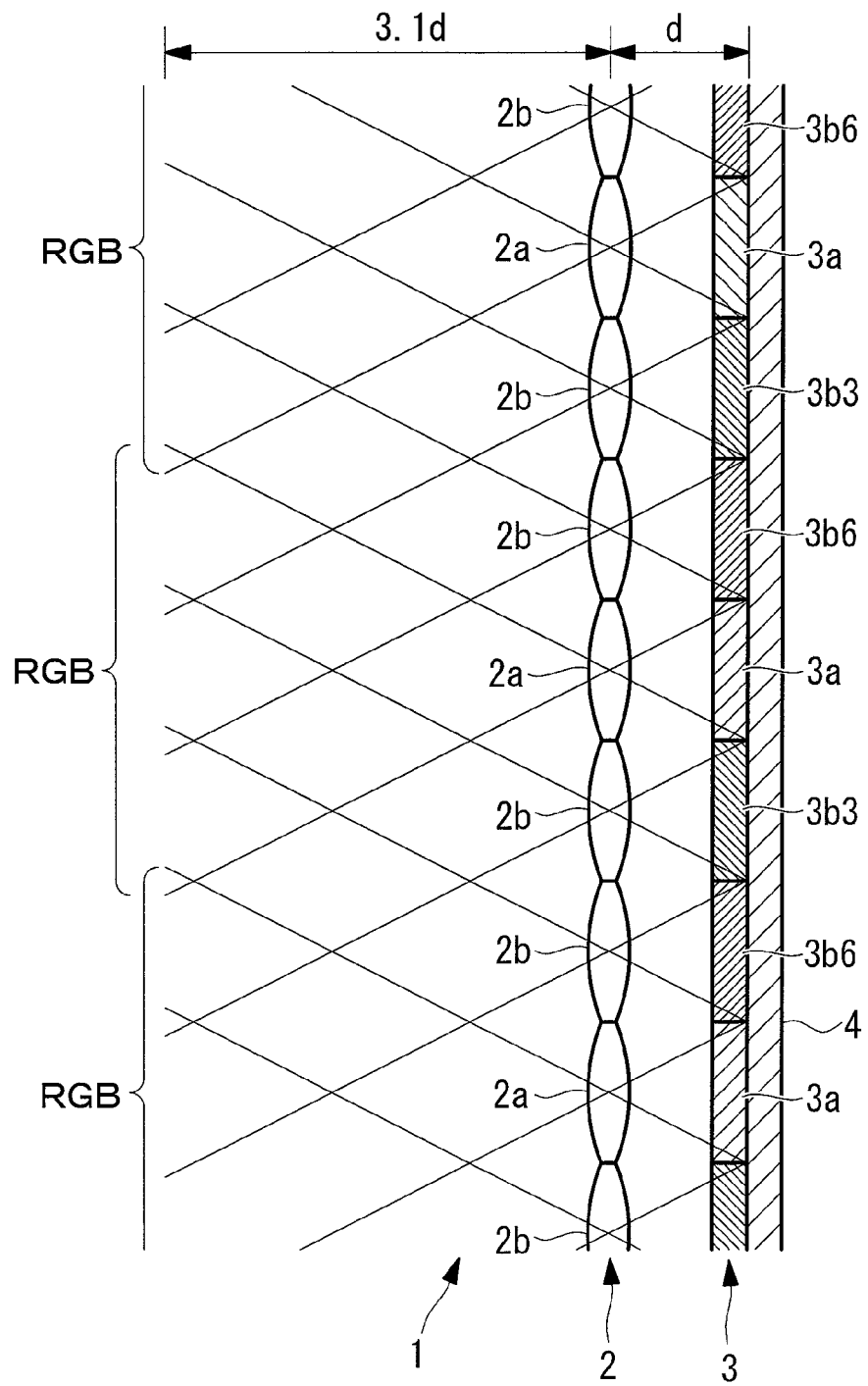
FIG. 9 is a longitudinal sectional view showing a modification of the image capturing module in FIG. 1.

Note that, in the image capturing module 1 according to this embodiment, it has been assumed that all of the microlenses 2a and 2b have the same optical characteristics, and that the reduction factor is set to 3; instead of this, however, a reduction factor slightly larger than 3, for example, 3.1 (though it is not limited thereto) may be used, as shown in FIG. 9. By doing so, it is possible to have portions that overlap with each other in the image of the subject obtained by the wavelength obtaining regions 4a and 4b of the same kind, and it is possible to more reliably prevent image loss.

Furthermore, the image capturing apparatus 10 according to this embodiment has been described in terms of an example in which the narrow-band-image processing portion 21 provided in the display-image generating portion 19 has the image combining portion 28 that combines the RGB image information and the selected narrow-band image information in a superimposed manner. Instead of this image combining portion 28, however, one having an image switching portion (not illustrated) that outputs the RGB image information and the narrow-band image information to the monitor 14 in an alternating manner may be employed. By doing so, even in the case where an image of a moving subject is acquired, it is possible to observe the subject without generating a positional shift between the alternating images.

Furthermore, although it has been assumed that, in the image capturing apparatus 10 described above, the wavelength selection portion 27 in the narrow-band-image processing portion 21 selects a single item of narrow-band image information, instead of this, it may select a plurality of items of narrow-band image information, which may be combined in the image combining portion 28. For example, when it is desired to create a melanin image, a hemoglobin image and so forth of the skin, it is possible to create such an image by combining a plurality of types of narrow-band images.

In addition, although a unit that creates a combined image in which RGB image information and narrow-band image information are superimposed has been illustrated as an example of the image combining portion 28, a unit that combines the RGB image information and the narrow-band image information in such a manner that they are displayed side-by-side may be employed.

Figure 10:
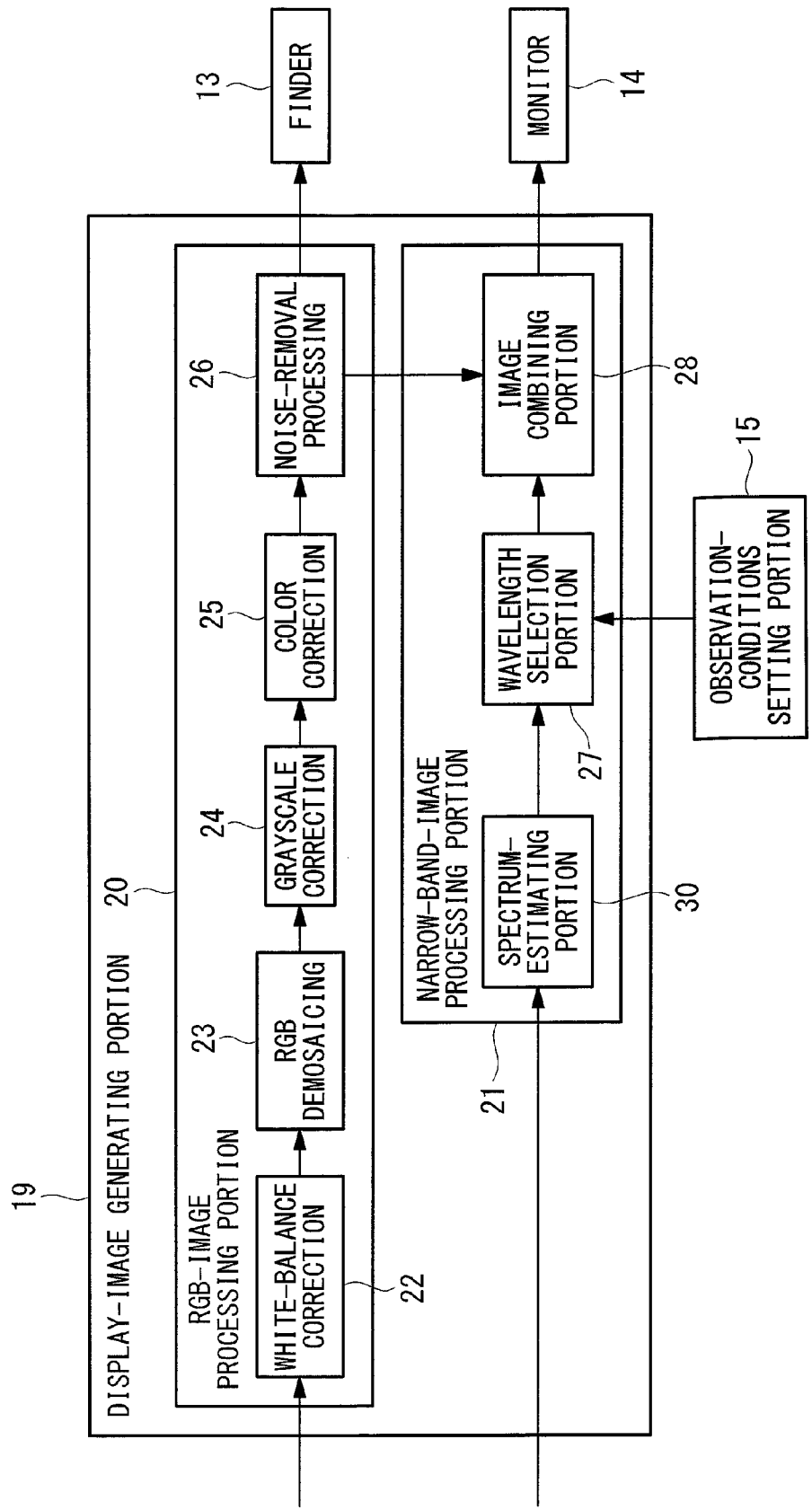
FIG. 10 is a block diagram showing a modification of the display-image generating portion in FIG. 6.

In addition, although it has been assumed that the image capturing module 1 obtains eight narrow-band images in this embodiment, as shown in FIG. 10, the narrow-band-image processing portion 21 may have a spectrum estimating portion 30 that estimates pixel values in other wavelength bands at each pixel from the acquired narrow-band images for the eight wavelength bands.

In other words, since the spectrum estimating portion 30 estimates the pixel value at each pixel in other wavelength bands based on the pixel values in eight different wavelength bands, even when a wavelength region other than the eight wavelength bands is specified in the wavelength selection portion 27, it is possible to select a narrow-band image in this other specified wavelength band by using pixel values estimated by the spectrum estimating portion 30.

Figure 11:
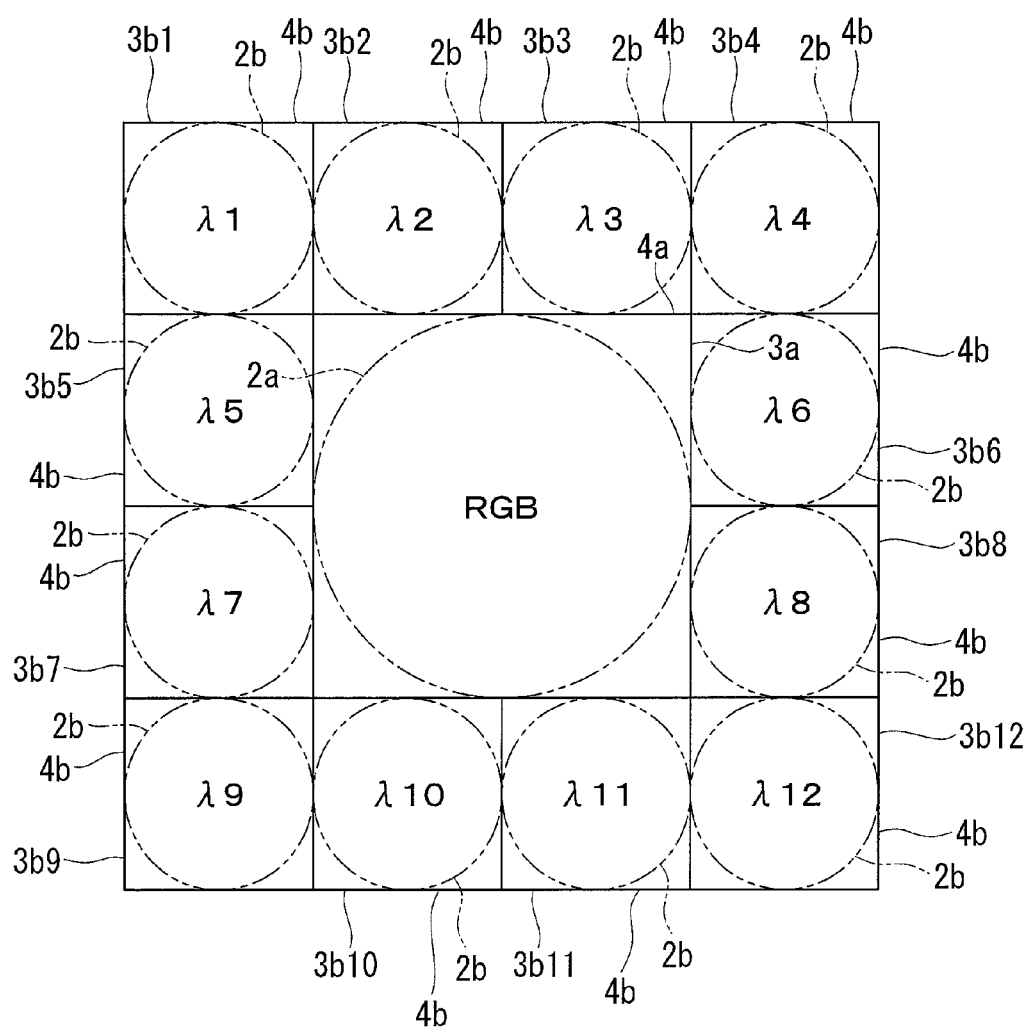
FIG. 11 is a diagram showing a modification of the image-capturing region unit and microlenses in FIG. 3.

In addition, although this embodiment has been described in terms of a case where all of the microlenses 2a and 2b have the same optical characteristics, as shown in FIG. 11, it is permissible to employ image-capturing region units PiQj formed of 4×4=16 partial regions 4a and 4b, and it is permissible to employ a configuration in which the color-wavelength obtaining region 4a is set to be four times larger than the narrow-band-wavelength obtaining regions 4b, and the microlens array 2 has different optical characteristics at the microlens 2a corresponding to the color-wavelength obtaining region 4a (first microlens) and the microlenses 2b corresponding to the narrow-band-wavelength obtaining regions 4b (second microlenses).

By doing so, it is possible to use ¼ of the pixels in the entire image capturing device 4 as the color-wavelength obtaining regions 4a, which makes it possible to improve the resolution of the obtained RGB image compared with the case shown in FIG. 3, where ⅑ of the pixels in the entire image capturing device 4 are used. In other words, it is possible to obtain an RGB image with higher resolution.

Figure 12:
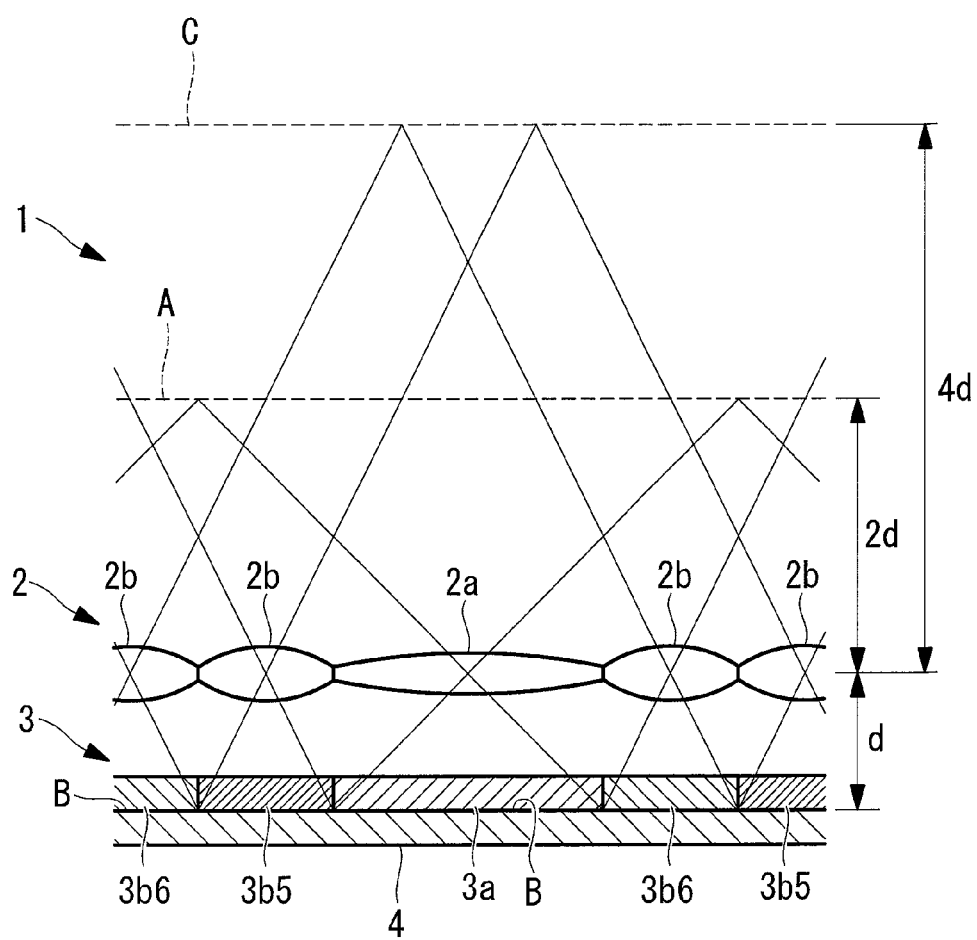
FIG. 12 is a longitudinal sectional view showing an image capturing module having the image-capturing region unit and microlenses in FIG. 11.

In this case, by using a microlens having a reduction factor of 2 as the first microlens 2a, as shown in FIG. 12, it is possible to obtain a lossless RGB image.

On the other hand, since loss would occur when using microlenses having a reduction factor of 2 as the second microlenses 2b, it is necessary to employ microlenses having a reduction factor of 4. Thus, as shown in FIG. 12, when the focal position of the first microlens 2a is coincident with the image plane A of the image capturing lens 11, as the RGB image, it is possible to obtain an image that is focused on the subject; in this case, however, the focal positions of the second microlenses 2b are disposed at another plane C shifted from the image plane A, resulting in an out-of-focus narrow-band image.

Such a configuration can be employed in the case where it is necessary to detect the presence or absence of a signal, without the need for high resolution, as in fluoroscopy. In addition, although the narrow-band-wavelength obtaining regions 4b constitute 1/16 of the entire image capturing device 4, resulting in ¼ of the resolution compared with the color-wavelength obtaining regions 4a, this configuration is effective in applications where high resolution is not necessary, such as fluoroscopy.

Figure 13:
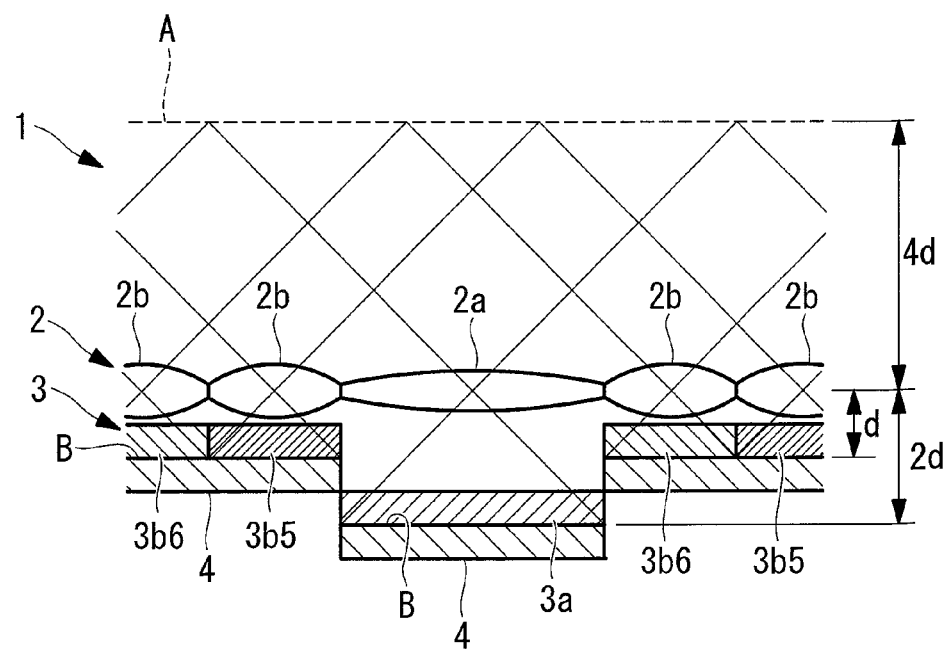
FIG. 13 is a longitudinal sectional view showing a first modification of the image capturing module in FIG. 12.
Figure 14:
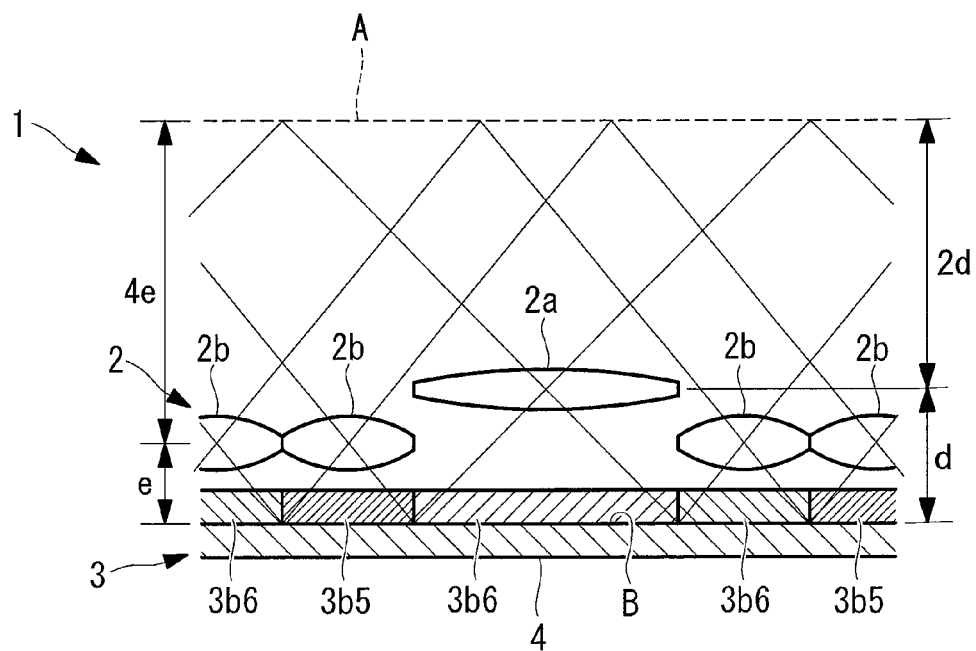
FIG. 14 is a longitudinal sectional view showing a second modification of the image capturing module in FIG. 12.

However, in cases where it is desirable to obtain an in-focus image also for the narrow-band image, as shown in FIG. 13 or FIG. 14, the positional relationships of the first microlens 2a and the second microlenses 2b in the optical-axis direction relative to the image capturing device 4 should be made different, so that the focal positions are all made coincident with the image plane A of the image capturing lens 11, while achieving reduction factors of 2 and 4, respectively.

In other words, in the example shown in FIG. 13, the positions of the first and second microlenses 2a and 2b in the optical-axis direction are all the same, and a step is provided at an image capturing plane B of the image capturing device 4 so that the positions of the color-wavelength obtaining region 4a and the narrow-band-wavelength obtaining regions 4b in the optical-axis direction are made to be different. In the example shown in FIG. 14, on the other hand, the image capturing plane B of the image capturing device 4 is entirely at the same position, and the positions of the first microlens 2a and the second microlenses 2b in the optical-axis direction are made to be different.

By doing so, the second microlenses, which have larger reduction factors and shorter focal lengths, are brought closer to the image capturing plane, making it possible to obtain an in-focus narrow-band image. In addition, making the positions of the microlenses 2a and 2b in the optical-axis direction all the same, as shown in FIG. 13, simplifies their fabrication.

Figure 15:
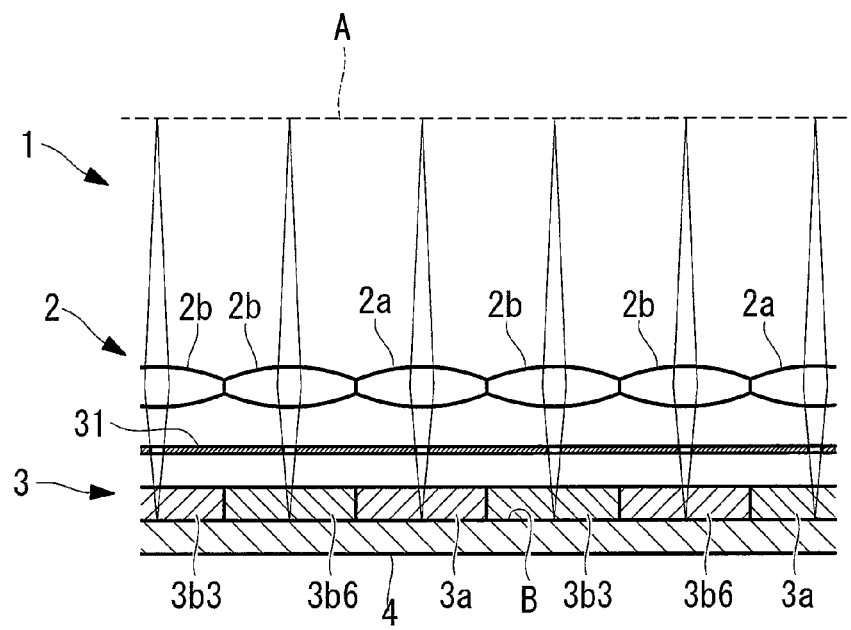
FIG. 15 is a longitudinal sectional view showing a first way of improving the spectral precision in etalons serving as the narrow-band filter portions.

In addition, in the embodiment described above, for the narrow-band filter portions 3b1 to 3b12 disposed at positions where they cover the narrow-band-wavelength obtaining regions 4b, although etalons have been given as examples, with an etalon, the wavelength that is transmitted changes according to the angle of incidence of the light, and therefore, it is preferable to make the light incident at an angle of incidence as close as possible to 90°. To achieve this, as shown in FIG. 15, apertures 31 may be provided between the microlenses 2a and 2b and the narrow-band filter portions 3b1 to 3b8, so that only light having an angle of incidence close to 90° in the incident light is made incident on the filter 3. Accordingly, it is possible to make the angle of incidence of the light that is incident on the narrow-band filter portions 3b1 to 3b12 close to 90°, so that light in the desired wavelength band can be allowed to pass therethrough with high precision.

Figure 16:
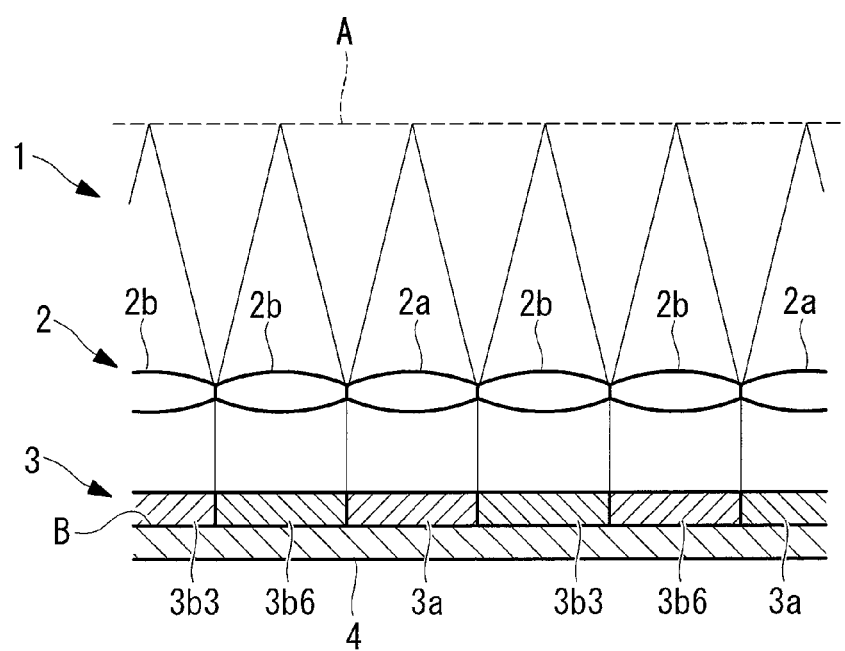
FIG. 16 is a longitudinal sectional view showing a second way of improving the spectral precision in etalons serving as the narrow-band filter portions.

As another method, microlenses that collimate the light from the subject and cause substantially collimated beams to be incident on the filter 3 may be employed as the microlenses 2a and 2b, as shown in FIG. 16. With this approach, too, it is possible to set the angle of incidence of the light falling on the filter 3 to substantially 90°.

Although the image capturing module 1 according to this embodiment has been illustrated in terms of image-capturing region units PiQj formed of 3×3 partial regions 4a and 4b and image-capturing region units PiQj formed of 4×4 partial regions 4a and 4b, in general, a configuration in which image-capturing region units PiQj formed of n×n (where n is an integer equal to or greater than 2) partial regions 4a and 4b are repeatedly arrayed may be used. Then, in the case where microlenses 2a and 2b corresponding to the partial regions 4a and 4b and whose size is $1/n^2$ the size of the entire image capturing device 4 are employed, if a reduction factor of n is used as the reduction factor of the microlenses 2a and 2b, it is possible to obtain a lossless image, and by employing microlenses 2a and 2b with a reduction factor larger than n, the images obtained by the neighboring wavelength obtaining regions 4a and 4b of the same kind can be made to partially overlap, thus achieving more reliable image loss prevention.

Although this embodiment has been illustrated in terms of an example case in which lossless signals are obtained for both the RGB image signal and the narrow-band image signal, it is possible to prevent loss for only the RGB signal, while permitting loss in the narrow-band image signal.

The image capturing apparatus 10 according to the present invention need not have the entire configurations shown in FIGS. 6 and 7; the advantageous effects of the present invention can be achieved so long as at least the image capturing module 1, the image-joining processing portion 17, and the image combining portion 28 are provided. In addition, the advantageous effects of the present invention can be achieved even if an image switching portion is provided instead of the image combining portion 28.

REFERENCE SIGNS LIST

A image plane
1 image capturing module
2 microlens array
2a first microlens
2b second microlens
3 filter
3a RGB filter portion
3b1-3b12 narrow-band filter portions
4 image capturing device
4a color-wavelength obtaining region
4b narrow-band-wavelength obtaining region
10 image capturing apparatus
15 observation-conditions setting portion
17 image-joining processing portion (RGB-image-information creating portion, narrow-band-image-information creating portion)
28 image combining portion
30 spectrum estimating portion
31 aperture

The invention claimed is:

1. An image capturing module comprising:
a microlens array that collects light from a subject which is imaged at an image plane;
a filter that allows light in specific wavelength bands in the light collected by the microlens array to pass therethrough; and
an image capturing device that acquires images of the light passing through the filter,
wherein the filter is formed by arraying a plurality of RGB filter portions that pass light in RGB wavelength bands and a plurality of narrow-band filter portions that pass light in wavelength bands that are narrower than the RGB wavelength bands,
wherein the image capturing device includes a plurality of color-wavelength obtaining regions that acquire images of the light passing through the plurality of RGB filter portions and a plurality of narrow-band-wavelength obtaining regions that acquire images of the light passing through the plurality of narrow-band filter portions,
wherein the microlens array includes a plurality of first microlenses that are disposed in correspondence with the respective plurality of color-wavelength obtaining regions and a plurality of second microlenses that are disposed in correspondence with the respective plurality of narrow-band-wavelength obtaining regions, and wherein the plurality of first microlenses are each disposed so that the light from the subject imaged at the image plane reaches at least one of the plurality of color-wavelength obtaining regions,
wherein in the image capturing device, a plurality of image-capturing region units are two dimensionally arrayed,
wherein each of the plurality of image-capturing region units includes one of the plurality of color-wavelength obtaining regions and $(n^2-1)$ of the plurality of narrow-band-wavelength obtaining regions in a square array of n rows and n columns, and
wherein the plurality of first microlenses and the plurality of second microlenses are arrayed with a ratio of $1:(n^2-1)$, wherein n is an integer equal to or greater than 2.

2. The image capturing module according to claim 1, wherein the plurality of color-wavelength obtaining regions and the plurality of narrow-band-wavelength obtaining regions have the same size, and wherein the plurality of first microlenses and the plurality of second microlenses have the same optical characteristics.

3. The image capturing module according to claim 1, wherein the plurality of first microlenses have a reduction factor greater than n.

4. An image capturing module comprising:
a microlens array that collects light from a subject which is imaged at an image plane;
a filter that allows light in specific wavelength bands in the light collected by the microlens array to pass therethrough; and
an image capturing device that acquires images of the light passing through the filter,
wherein the filter is formed by arraying a plurality of RGB filter portions that pass light in RGB wavelength bands and a plurality of narrow-band filter portions that pass light in wavelength bands that are narrower than the RGB wavelength bands, wherein the image capturing device includes a plurality of color-wavelength obtaining regions that acquire images of the light passing through the plurality of RGB filter portions and a plurality of narrow-band-wavelength obtaining regions that acquire images of the light passing through the plurality of narrow-band filter portions, wherein the microlens array includes a plurality of first microlenses that are disposed in correspondence with the respective plurality of color-wavelength obtaining regions and a plurality of second microlenses that are disposed in correspondence with the respective plurality of narrow-band-wavelength obtaining regions, and wherein the plurality of first microlenses are each disposed so that the light from the subject imaged at the image plane reaches at least one of the plurality of color-wavelength obtaining regions, wherein each of the plurality of color-wavelength obtaining regions is formed to be larger than each of the plurality of narrow-band-wavelength obtaining regions, and wherein each of the plurality of first microlenses has a reduction factor smaller than that of each of the plurality of second microlenses.

5. The image capturing module according to claim 4, wherein each of the plurality of first microlenses is disposed at a position separated from an image capturing plane of the image capturing device by a distance greater than that of each of the plurality of second microlenses.

6. The image capturing module according to claim 5, wherein a step is provided between an image capturing plane of the image capturing device corresponding to each of the plurality of color-wavelength obtaining regions and an image capturing plane of the image capturing device corresponding to each of the plurality of narrow-band-wavelength obtaining regions.

7. The image capturing module according to claim 1, further comprising an aperture disposed between each of the plurality of second microlenses and each of the plurality of narrow-band filter portions.

8. The image capturing module according to claim 1, wherein each of the plurality of second microlenses collects the light from the subject and makes the light incident on the plurality of narrow-band filter portions in the form of substantially collimated light.

9. An image capturing apparatus comprising:
a microlens array that collects light from a subject which is imaged at an image plane;
a filter that allows light in specific wavelength bands in the light collected by the microlens array to pass therethrough; and
an image capturing device that acquires images of the light passing through the filter,
wherein the filter is formed by arraying a plurality of RGB filter portions that pass light in RGB wavelength bands and a plurality of narrow-band filter portions that pass light in wavelength bands that are narrower than the RGB wavelength bands,
wherein the image capturing device includes a plurality of color-wavelength obtaining regions that acquire images of the light passing through the plurality of RGB filter portions and a plurality of narrow-band-wavelength obtaining regions that acquire images of the light passing through the plurality of narrow-band filter portions,
wherein the microlens array includes a plurality of first microlenses that are disposed in correspondence with the respective plurality of color-wavelength obtaining regions and a plurality of second microlenses that are disposed in correspondence with the respective plurality of narrow-band-wavelength obtaining regions, and
wherein the plurality of first microlenses are each disposed so that the light from the subject imaged at the image plane reaches at least one of the plurality of color-wavelength obtaining regions, and
wherein the image capturing apparatus further comprising:
an RGB-image-information creating portion that creates RGB image information by combining image information obtained by the plurality of color-wavelength obtaining regions in the image capturing device;
a narrow-band-image-information creating portion that creates narrow-band image information by combining image information obtained by the plurality of narrow-band-wavelength obtaining regions in the image capturing device; and
an image combining portion that combines the narrow-band image information created by the narrow-band-image-information creating portion and the RGB image information created by the RGB-image-information creating portion.

10. The image capturing apparatus according to claim 9, wherein the narrow-band-image-information creating portion includes a spectrum estimating portion that estimates a spectrum of pixel values at each pixel based on the image information of a plurality of wavelength bands obtained for the same pixels by a narrow-band-wavelength obtaining region in the image capturing module and an observation-conditions setting portion that sets a wavelength band desired to be observed, and
wherein the narrow-band-image-information creating portion creates the narrow-band image information by selecting, pixel values of the wavelength band set in the observation-conditions setting portion at each pixel, from the spectrum estimated in the spectrum estimating portion.

11. An image capturing apparatus comprising:
a microlens array that collects light from a subject which is imaged at an image plane;
a filter that allows light in specific wavelength bands in the light collected by the microlens array to pass therethrough; and
an image capturing device that acquires images of the light passing through the filter,
wherein the filter is formed by arraying a plurality of RGB filter portions that pass light in RGB wavelength bands and a plurality of narrow-band filter portions that pass light in wavelength bands that are narrower than the RGB wavelength bands,
wherein the image capturing device includes a plurality of color-wavelength obtaining regions that acquire images of the light passing through the plurality of RGB filter portions and a plurality of narrow-band-wavelength obtaining regions that acquire images of the light passing through the plurality of narrow-band filter portions,
wherein the microlens array includes a plurality of first microlenses that are disposed in correspondence with the respective plurality of color-wavelength obtaining regions and a plurality of second microlenses that are disposed in correspondence with the respective plurality of narrow-band-wavelength obtaining regions, and wherein the plurality of first microlenses are each disposed so that the light from the subject imaged at the image plane reaches at least one of the plurality of color-wavelength obtaining regions, and wherein the image capturing apparatus further comprises:

an RGB-image-information creating portion that creates RGB image information by combining image information obtained by the plurality of color-wavelength obtaining regions in the image capturing module;

a narrow-band-image-information creating portion that creates narrow-band image information by combining image information obtained by the plurality of narrow-band-wavelength obtaining regions in the image capturing module; and an image switching portion that alternately outputs the narrow-band image information created by the narrow-band-image-information creating portion and the RGB image information created by the RGB-image-information creating portion.

12. The image capturing apparatus according to claim 11, wherein the narrow-band-image-information creating portion includes a spectrum estimating portion that estimates a spectrum of pixel values at each pixel based on the image information of a plurality of wavelength bands obtained for the same pixels by a narrow-band-wavelength obtaining region in the image capturing device and an observation-conditions setting portion that sets a wavelength band desired to be observed, and wherein the narrow-band-image-information creating portion creates the narrow-band image information by selecting, pixel values of the wavelength band set in the observation-conditions setting portion at each pixel, from the spectrum estimated in the spectrum estimating portion.

* * * * *